United States Patent
Hess (10) Patent No.: US 9,390,494 B2
(45) Date of Patent: Jul. 12, 2016

(54) DELTA DIE INTENSITY MAP MEASUREMENT

(71) Applicant: KLA-Tencor Corporation, Milpitas, CA (US)

(72) Inventor: Carl E. Hess, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 264 days.

(21) Appl. No.: 14/101,712

(22) Filed: Dec. 10, 2013

(65) Prior Publication Data

US 2014/0168418 A1    Jun. 19, 2014

Related U.S. Application Data

(60) Provisional application No. 61/736,721, filed on Dec. 13, 2012.

(51) Int. Cl.
*G06T 7/00* (2006.01)
*G01N 21/956* (2006.01)

(52) U.S. Cl.
CPC .......... *G06T 7/001* (2013.01); *G01N 21/95607* (2013.01); *G01N 2021/95615* (2013.01); *G06T 2207/10056* (2013.01); *G06T 2207/20021* (2013.01); *G06T 2207/30148* (2013.01)

(58) Field of Classification Search
CPC ............. G01N 2021/95615; G01N 21/95607; G06T 2207/10056; G06T 2207/20021; G06T 2207/30148; G06T 7/001
USPC .................... 348/125, 126, 129; 382/144, 149
See application file for complete search history.

(56) References Cited

U.S. PATENT DOCUMENTS

| 6,614,520 B1 | 9/2003 | Bareket et al. |
| 7,069,155 B1 | 6/2006 | Phan et al. |

(Continued)

FOREIGN PATENT DOCUMENTS

| JP | 2004271421 A | 9/2004 |
| JP | 2005300884 A | 10/2005 |

(Continued)

OTHER PUBLICATIONS

"International Application Serial No. PCT/US2013/074841, Search Report and Written Opinion mailed Sep. 25, 2014", 12 pgs.

(Continued)

*Primary Examiner* — Jay Patel
*Assistant Examiner* — Francis G Geroleo
(74) *Attorney, Agent, or Firm* — Kwan & Olynick LLP (57) ABSTRACT

With an optical inspection tool, images of a plurality of patches of a plurality of dies of a reticle are obtained. The patch images are obtained so that each patch image is positioned relative to a same reference position within its respective die as another die-equivalent one of the patch images in each the other ones of the dies. For each patch image, an integrated value is determined for an image characteristic of sub-portions of such patch image. For each patch image, a reference value is determined based on the integrated values of the patch image's corresponding die-equivalent patch images. For each patch image, a difference between that patch image's integrated value and an average or median value of its die-equivalent patch images is determined whereby a significant difference indicates a variance in a pattern characteristic of a patch and an average or median pattern characteristic of its die-equivalent patches.

26 Claims, 8 Drawing Sheets

(56) References Cited

U.S. PATENT DOCUMENTS

| | | |
|---|---|---|
| 7,126,681 B1 | 10/2006 | Chen et al. |
| 7,564,545 B2 | 7/2009 | Stokowski |
| 7,586,607 B2 * | 9/2009 | Sun .................. G01N 21/88 356/237.2 |
| 8,611,639 B2 * | 12/2013 | Kulkarni ............ G01N 21/9501 382/145 |
| 2002/0085297 A1 | 7/2002 | Boettiger et al. |
| 2002/0131052 A1 | 9/2002 | Emery |
| 2003/0174876 A1 | 9/2003 | Eran et al. |
| 2005/0002020 A1 | 1/2005 | Inoue et al. |
| 2005/0166171 A1 | 7/2005 | Bartov |
| 2005/0174570 A1 | 8/2005 | Kvamme et al. |
| 2008/0170773 A1 | 7/2008 | Wihl et al. |
| 2008/0304056 A1 | 12/2008 | Alles et al. |
| 2009/0037134 A1 | 2/2009 | Kulkarni et al. |
| 2009/0041332 A1 * | 2/2009 | Bhaskar .............. G01N 21/93 382/145 |
| 2009/0226076 A1 | 9/2009 | Sakai et al. |
| 2010/0074516 A1 * | 3/2010 | Kawaragi ............ G01N 21/956 382/149 |
| 2010/0215247 A1 * | 8/2010 | Kitamura .............. G06T 7/001 382/149 |
| 2011/0014577 A1 | 1/2011 | Hashimoto |
| 2011/0235905 A1 | 9/2011 | Yokokawa |
| 2012/0002860 A1 * | 1/2012 | Sakai .................. G06T 7/001 382/149 |
| 2012/0020546 A1 * | 1/2012 | Inoue .............. G01N 21/95607 382/145 |
| 2012/0137260 A1 * | 5/2012 | Pang ...................... G03F 1/68 716/52 |
| 2013/0028505 A1 * | 1/2013 | Dmitriev .................. G03F 1/84 382/144 |
| 2013/0211736 A1 | 8/2013 | Hess et al. |
| 2015/0103351 A1 | 4/2015 | Hess et al. |

FOREIGN PATENT DOCUMENTS

| | | |
|---|---|---|
| JP | 2006018054 A | 1/2006 |
| JP | 2006080437 A | 3/2006 |
| KR | 1020100069503 A | 6/2010 |
| WO | 2011035946 A1 | 3/2011 |
| WO | 2012012265 A2 | 1/2012 |
| WO | 2013142079 A1 | 9/2013 |

OTHER PUBLICATIONS

"Int'l Application Serial No. PCT/US2013/029587, Preliminary Report on Patentability mailed Oct. 2, 2014", 8 pgs.

"International Application Serial No. PCT/US2013/026224, Search Report and Written Opinion mailed Jun. 3, 2013", 11 pgs.

"Int'l Application Serial No. PCT/US2013/029587, Search Report and Written Opinion mailed Jun. 24, 2013", 9 pgs.

Sagiv, Amir et al., "IntenCD: Mask Critical Dimension Variation Mapping", Proc. of SPIE vol. 7028, 70282X, Retrieved from the Internet: < http://proceedings.spiedigitallibrary.org/ on Jan. 14, 2013 Terms of Use: http://spiedl.org/terms >, Accessed on Jan. 14, 2013, 2008, 12 pgs.

U.S. Appl. No. 13/757,103, Non Final Office Action mailed Dec. 21, 2015, 26 pgs.

U.S. Appl. No. 14/381,304, Non Final Office Action mailed Nov. 2, 2015, 10 pgs.

European Application Serial No. 13763512.4, Supplementary Search Report and Search Opinion mailed Nov. 23, 2015, 6 pgs.

* cited by examiner

DELTA DIE INTENSITY MAP MEASUREMENT

CROSS-REFERENCE TO RELATED APPLICATIONS

This application claims priority under 35 U.S.C. §119 of prior U.S. Provisional Application No. 61/736,721, filed 13 Dec. 2012, titled "Delta Die Intensity Map Measurement" by Carl E. Hess, which application is herein incorporated by reference in its entirety for all purposes.

TECHNICAL FIELD OF THE INVENTION

The invention generally relates to the field of reticle inspection. More particularly the present invention relates to a method to detect reticle CD variation.

BACKGROUND

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the fabricated devices have become increasingly sensitive to defects. That is, defects which cause faults in the device are becoming increasingly smaller. The device needs to be fault free prior to shipment to the end users or customers.

An integrated circuit is typically fabricated from a plurality of reticles. Generation of reticles and subsequent optical inspection of such reticles have become standard steps in the production of semiconductors. Initially, circuit designers provide circuit pattern data, which describes a particular integrated circuit (IC) design, to a reticle production system, or reticle writer. The circuit pattern data is typically in the form of a representational layout of the physical layers of the fabricated IC device. The representational layout includes a representational layer for each physical layer of the IC device (e.g., gate oxide, polysilicon, metallization, etc.), wherein each representational layer is composed of a plurality of polygons that define a layer's patterning of the particular IC device.

The reticle writer uses the circuit pattern data to write (e.g., typically, an electron beam writer or laser scanner is used to expose a reticle pattern) a plurality of reticles that will later be used to fabricate the particular IC design. A reticle inspection system may then inspect the reticle for defects that may have occurred during the production of the reticles or after use of the reticle.

Thus, there is a continuing need for improved techniques for inspecting reticles and the like.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method of inspecting a photolithographic reticle is disclosed. With an optical inspection tool, a plurality of patch images of a plurality of patches of a plurality of dies of the reticle is obtained. The dies are designed to be identical, and the patch images are obtained so that each patch image is positioned relative to a same reference position within its respective die as another die-equivalent one of the patch images in each of a plurality of other ones of the dies. For each patch image, an integrated value is determined for an image characteristic of a plurality of sub-portions of such patch image. For each patch image, a reference value is determined based on the integrated values of the patch image's corresponding die-equivalent patch images. For each patch image, a difference between that patch image's integrated value and an average or median value of the integrated values of the patch image's die-equivalent patch images is determined whereby such difference indicates a difference between a pattern characteristic of any patch and an average or median pattern characteristic of its die-equivalent patches.

In a specific implementation, the pattern characteristic is a critical dimension. In another aspect, the patch images are obtained by using the optical tool to scan an optical beam along a plurality of swaths that include all the dies of the reticle. In another embodiment, each image patch's reference position corresponds to a die edge of such image patch's corresponding die and the patch images are obtained by positioning a portion of the swaths at the die edge a corresponding die. In another example, the patch images are obtained from a single swath selected from a plurality of swaths that were imaged with the optical tool by scanning an optical beam along each of the swaths, and the single swath includes portions of a subset of all the dies of the reticle, wherein the subset of dies are aligned with each other and in a direction in which the optical beam scans along the single swath.

In another aspect, the integrated value for each patch image is an average of a plurality of intensity values of the sub-portions of such patch image. In another embodiment, the integrated value for each patch image is a median of a plurality of intensity values of the sub-portions of such patch image. In another implementation, each integrated value is an average of both reflected and transmitted intensity values from each corresponding patch image. In a further aspect, the method includes generating a delta intensity map based on the determined differences. In a further aspect, the delta intensity map indicates a standard deviation of each determined difference. In yet a further aspect, the method includes defining any standard deviations that is above a predefined threshold as a critical dimension variation defect. In another embodiment, each determined difference includes a reflected intensity difference value and a transmitted difference value, and the delta intensity map is generated by combining each reflected difference value with its corresponding transmitted difference value.

In another example, combining each reflected difference value with its corresponding transmitted difference value is performed by averaging each reflected difference value with its corresponding transmitted difference value (e.g., by subtracting each reflected difference value from its corresponding transmitted value and dividing by two). In a further aspect, combining each reflected difference value with its corresponding transmitted difference value includes weighting each reflected difference value differently from its corresponding transmitted difference value. In another example, the method includes providing a dose correction for a photolithography process that uses the reticle based on the delta intensity map. In another aspect, each reference value is determined by first excluding any integrated values that has a standard deviation that is greater than a predefined value from the reference value determination. In yet another implementation, the patch images are obtained by using the optical tool in an aerial mode.

In certain embodiments, the invention pertains to a system for inspecting a photolithographic reticle. The system includes at least one memory and at least one processor that are configured to perform at least some of the above described operations. In other embodiments, the invention pertains to computer readable media having instructions stored thereon for performing at least some of the above described operations.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Certain embodiments of the present invention provide techniques and systems for inspecting a reticle to detect defects or variations in critical dimension (CD) of reticle features. Although the following example embodiments are described with respect to a reticle, any suitable type of sample may be monitored using such techniques or systems. Additionally, the following example embodiments can be applied to the monitoring of other sample characteristics, besides CD variation.

A "reticle" generally includes a transparent substrate, such as glass, borosilicate glass, quartz, or fused silica having a layer of opaque material formed thereon. The opaque (or substantially opaque) material may include any suitable material that completely or partially blocks photolithographic light (e.g., deep UV). Example materials include chrome, molybdenum silicide (MoSi), tantalum silicide, tungsten silicide, opaque MoSi on glass (OMOG), etc. A polysilicon film may also be added between the opaque layer and transparent substrate to improve adhesion. A low reflective film, such as molybdenum oxide ($MoO_2$), tungsten oxide ($WO_2$), titanium oxide ($TiO_2$), or chromium oxide ($CrO_2$) may be formed over the opaque material.

The term reticle refers to different types of reticles including, but not limited to, a clear-field reticle, a dark-field reticle, a binary reticle, a phase-shift mask (PSM), an alternating PSM, an attenuated or halftone PSM, a ternary attenuated PSM, and a chromeless phase lithography PSM. A clear-field reticle has field or background areas that are transparent, and a dark-field reticle has field or background areas that are opaque. A binary reticle is a reticle having patterned areas that are either transparent or opaque. For example, a photomask made from a transparent fused silica blank with a pattern defined by a chrome metal adsorbing film can be used. Binary reticles are different from phase-shift masks (PSM), one type of which may include films that only partially transmit light, and these reticles may be commonly referred to as halftone or embedded phase-shift masks (EPSMs). If a phase-shifting material is placed on alternating clear spaces of a reticle, the reticle is referred to as an alternating PSM, an ALT PSM, or a Levenson PSM. One type of phase-shifting material that is applied to arbitrary layout patterns is referred to as an attenuated or halftone PSM, which may be fabricated by replacing the opaque material with a partially transmissive or "halftone" film. A ternary attenuated PSM is an attenuated PSM that includes completely opaque features as well.

In general, the opaque, absorbing, partially opaque, phase-shifting material is formed into pattern structures that are designed and formed with critical dimension (CD) widths, which also results in clear spaces between the structures that also have a CD. A particular CD value may generally affect how a particular reticle feature is transferred to the wafer in the photolithography process and such CD is chosen to optimize this transfer process. Said in another way, if a certain reticle feature's CD value is within a specified CD range, such CD value will result in fabrication of a corresponding wafer feature that allows proper operation of the resulting integrated circuit, as intended by the circuit designer. Features are typically formed with minimum dimensions that also result in operational circuits so as to conserve integrated chip area.

A newly fabricated reticle may include CD (or other film or pattern characteristic) defect issues. For example, the reticle may have defective CD regions, such as mask-writer swath-errors. A reticle may also become damaged over time in a number of different ways. In a first degradation example, the photolithographic exposure process may result in physical degradation of the opaque material of the reticle. For instance, a high power beam, such as a high powered deep ultra violet (UV) beam at 193 nm, that is used on the reticle may physically cause damage to the opaque material on the reticle. Damage may also be caused by other wavelengths, such as a 248 nm UV beam. In effect, the UV beam can physically cause the opaque patterns on the reticle to slump by blasting the corners off of opaque features and causing the features to flatten. As a result, opaque features may have significantly larger CD widths, as compared to original CD widths, while the spacings between such opaque features may have a much smaller CD width, as compared with the original CD width. This type of degradation is referred to as "chrome" degradation since this type of problem typically occurs in chrome type reticles. Other types of CD degradation may be caused by chemical reactions between the reticle features (MoSi) and the exposure light, cleaning processes, contamination, etc. These physical effects can also adversely affect the critical dimensions (CD's) of the reticle over time.

As a result of this degradation, the feature CD values may have significantly changed so as to affect wafer yield. For instance, mask feature widths may be significantly larger than the original line width CD.

For masks with highly repetitive patterns, such as masks for memory chips, broad scale reflected or transmitted intensity maps may be generated from a reticle inspection system to show CD variations. To generate such maps, the intensity of a local area with repeating patterns is compared to the full-plate average of those same repeating structures on the mask. Such a technique may not work effectively on logic (non-memory) masks because the pattern is varying across the mask. One cannot use one arbitrary region of the mask as a reference for a different region since the compared regions typically contain different patterns.

Figure 1:
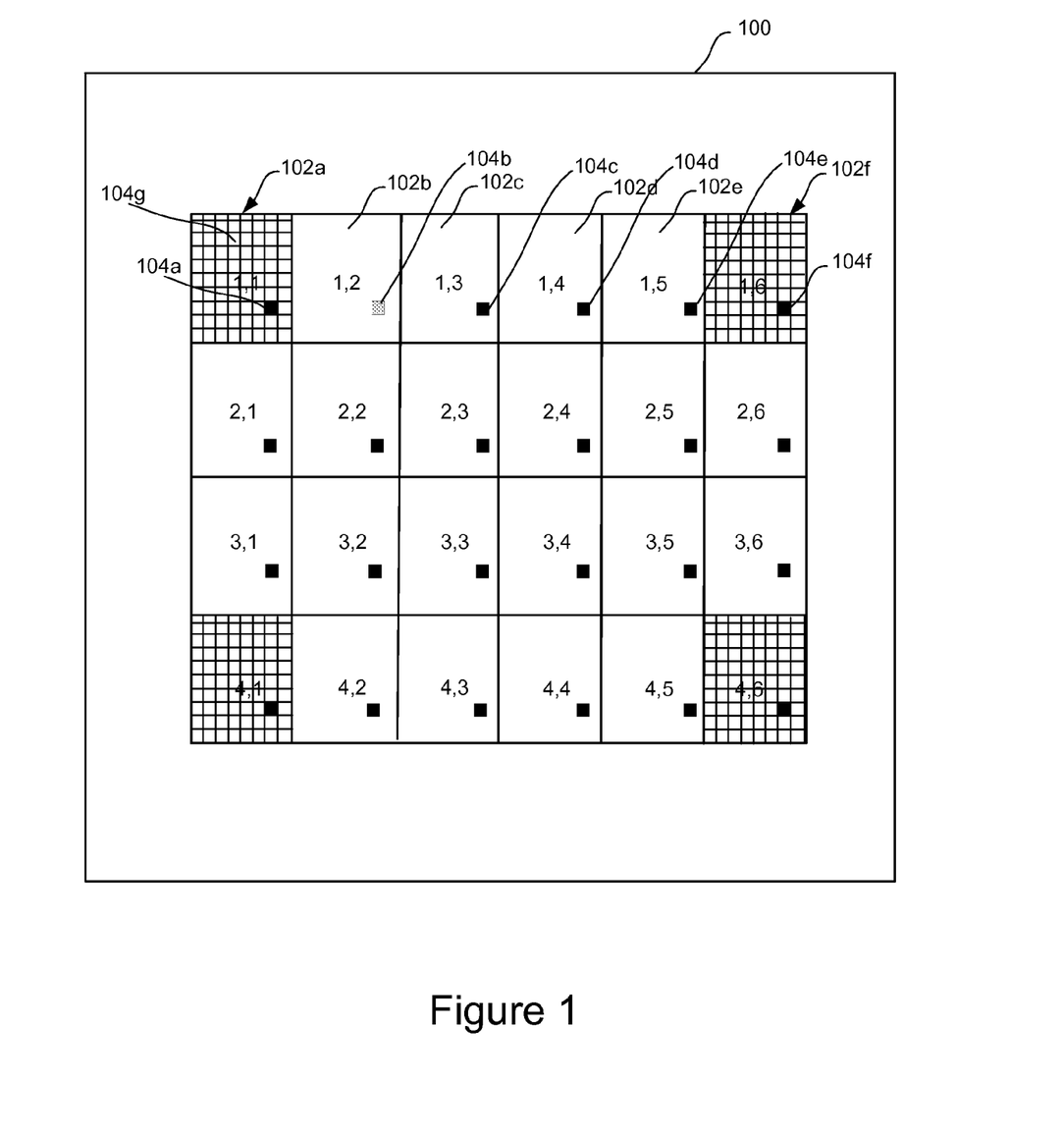
FIG. 1 is a diagrammatic top view of an example reticle having a plurality of dies for which inspection techniques may be implemented in accordance with one embodiment of the present invention.

FIG. 1 is a diagrammatic top view of an example reticle 100 having a plurality of dies for which inspection techniques may be implemented in accordance with one embodiment of the present invention. As shown, the reticle includes a 6 by 4 array of dies that are designated by row and column. For instance, dies 102a~102f in the first top row are designated (1,1), (1,2), (1,3), (1,4), (1,5), and (1,6), from the leftmost column to the rightmost column, respectively. Similarly, the dies of the last row have designations (4,1), (4,2), (4,3), (4,4), (4,5), and (4,6) for each specific row and column.

Although the dies contain logic patterns as opposed to repeating memory patterns, the dies are designed to be identical to each other. Accordingly, each die portion (referred to as a "patch") of a particular die is expected to be identical to at least one other patch from each of the other dies. Different patches from different dies that designed to be identical are referred to herein as "die-equivalent." For instance, patch 104b of die 102b has die-equivalent patches (e.g, 104a, 104c, 104d, 104e, and 104f) in the other dies (e.g., 102a, 102c, 102d, 102e, and 102f).

During inspection, a plurality of patch images of the patches of the reticle, including the dies, may be obtained using an optical inspection tool. During image acquisition, multiple patch images are obtained for each die. For instance, image patches are obtained for patches 102a and 102g of die 102a. In certain embodiments of the present invention, the image patches are obtained so as to result in die-equivalent patches across the dies, and the die-equivalent patches are processed to detect CD defects or CD variation.

In a specific embodiment, the intensity value for each test patch is compared to an average intensity of the test patch's corresponding die-equivalent patches to obtain a delta map that indicates CD variation across the reticle. The intensity value of each patch may be obtained by averaging reflected and/or transmitted intensity values of the patch's pixels. If the reticle pattern of die-equivalent patches are identical and do not vary in CD (or any other pattern characteristic), the transmitted or reflected light from the die-equivalent patches is expected to be the same. If the reflected or transmitted intensity for a particular patch differs from the other die-equivalent patches, it may be inferred that the pattern of the particular patch has a CD variation as compared to the its die-equivalent patches. For example, an increase in the transmitted intensity infers that the CD of the opaque reticle pattern has decreased and the CD of the clear reticle area has increased.

Figure 2:
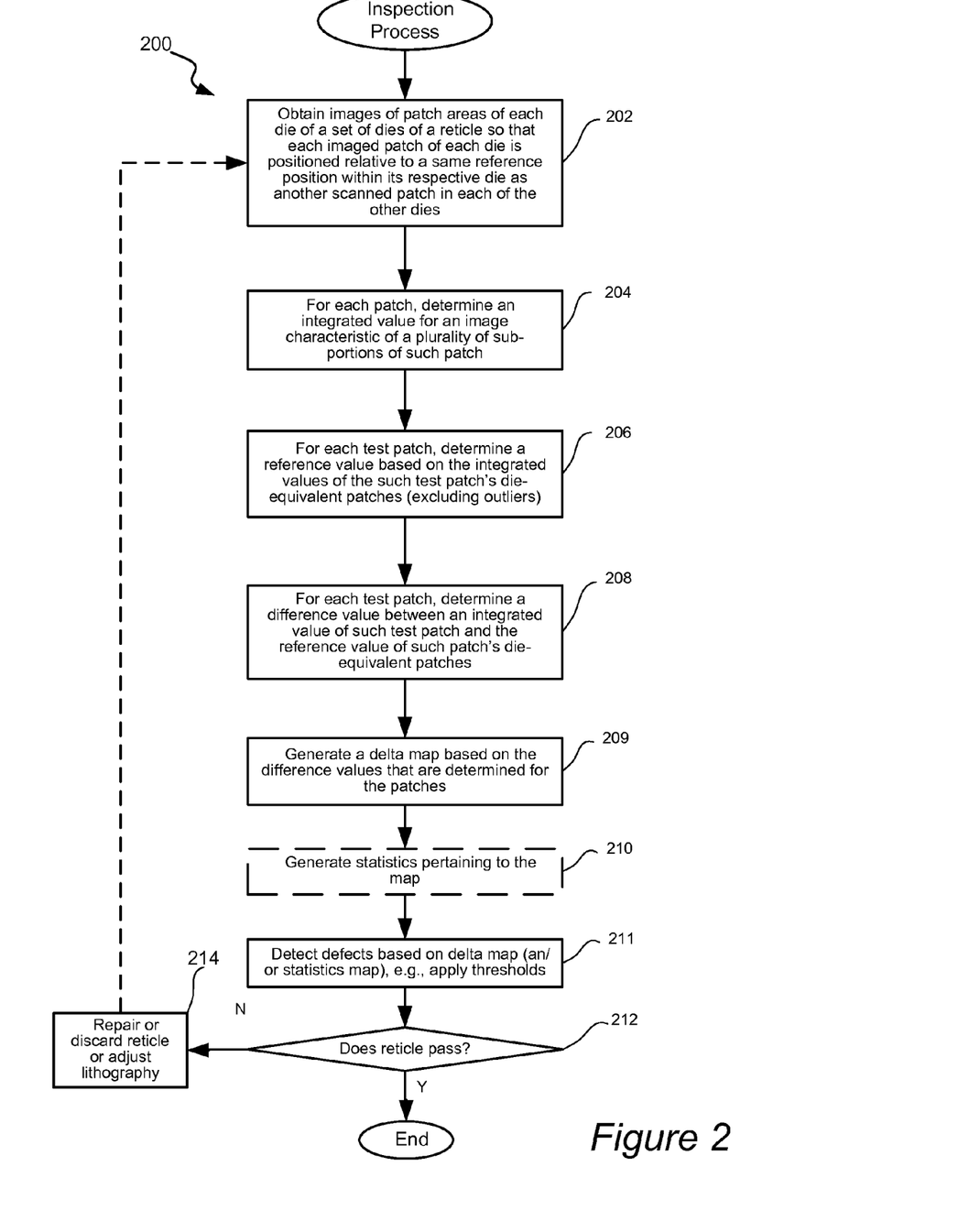
FIG. 2 is a flow chart illustrating an inspection procedure that utilizes die-equivalent image patches in accordance with one embodiment of the present invention.

FIG. 2 is a flow chart illustrating an inspection procedure that utilizes die-equivalent patch images in accordance with one embodiment of the present invention. The following inspection process 200 may be performed on a newly fabricated reticle so as to detect fabrication defective areas or performed on a reticle that has been used one or more times in a photolithography process so as to detect degradation.

Die-equivalent patches may be obtained in any suitable manner as described further below. In the illustrated embodiment, images of patch areas of each die of a set of dies of a reticle are obtained so that each imaged patch of each die is positioned relative to a same reference position within its respective die as another scanned patch in each of the other dies in operation 202.

Figure 3A:
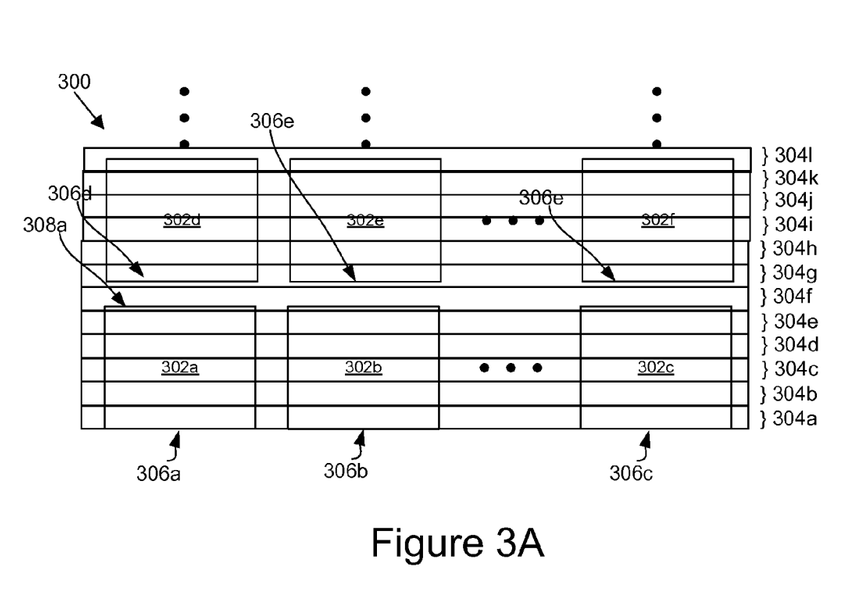
FIG. 3A is a diagrammatic representation of a plurality of scan "swaths" of a reticle portion in accordance with a first implementation of the present invention.

In a first implementation, each set of die-equivalent patches are obtained from a same scanned swath of patches. FIG. 3A is a diagrammatic representation of a plurality of scanned/imaged "swaths" (e.g., 304a~304l) of a reticle portion 300 in accordance with embodiment of the present invention. Each set of die-equivalent intensity data may correspond to a "swath" of the reticle portion 300. Each set of die-equivalent intensity data may be obtained by sequentially scanning swaths from the reticle in a serpentine or raster pattern. For example, the first swath 304a of the reticle portion 300 is scanned by an optical beam of an optical inspection system from left to right to obtain a first set of intensity data. The second swath 304b is then scanned from right to left to obtain a second set of intensity data. Swaths are sequentially scanned from the bottom row of dies through the top row of dies.

Figure 3B:
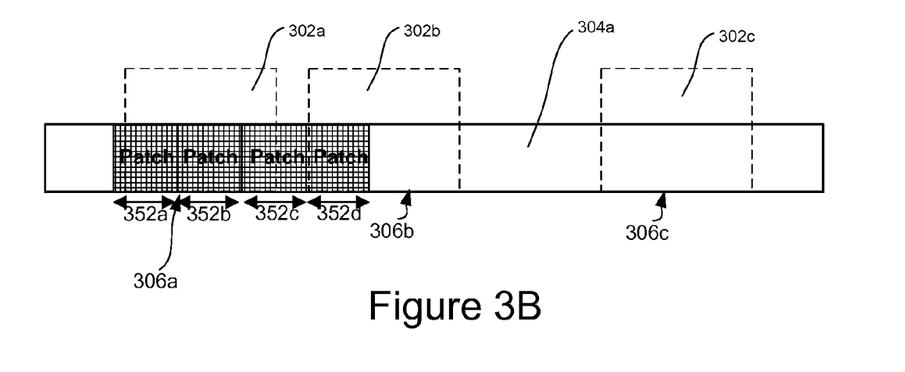
FIG. 3B is a diagrammatic illustration of an intensity data set that corresponds to a reticle swath that is divided into patches in accordance with a specific implementation.

FIG. 3B is a diagrammatic illustration of an intensity data set that corresponds to swath 302a. The intensity data for reticle swath 304a is also divided into a plurality of intensity data sets that correspond to a plurality of patches (e.g., 352a, 352b, 352c, and 352d). Intensity data may be collected for multiple points in each patch of each swath.

Each scanned swath will contain die-equivalent patches of the entire swath, including the patches, that are each positioned relative to a same reference position in its corresponding dies for which the swath is obtained. As shown, the swath 304a and its patches are positioned with respect to a bottom edge of each patch's respective die (e.g., bottom edges 306a~306c of dies 302a~302b, respectively).

In this first implementation, die-equivalent patches of only a single swath are processed together. After the entire reticle is imaged, the image analysis operations of FIG. 2 may be repeated for each imaged set of die-equivalent patches (e.g., each swath row) of the reticle.

Figure 3C:
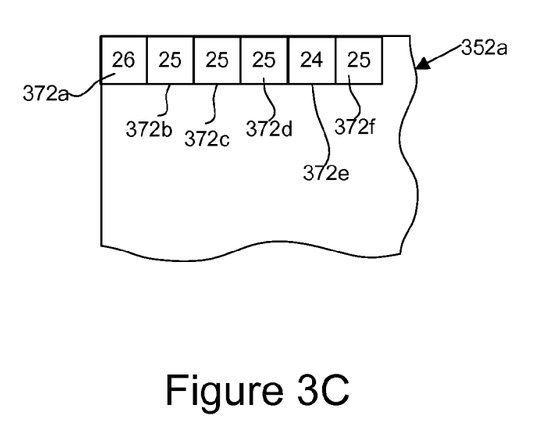
FIG. 3C is a diagrammatic illustration of multiple intensity data sets that corresponds to multiple local areas of each patch of a swath of the reticle in accordance with an example implementation.
Figure 3D:
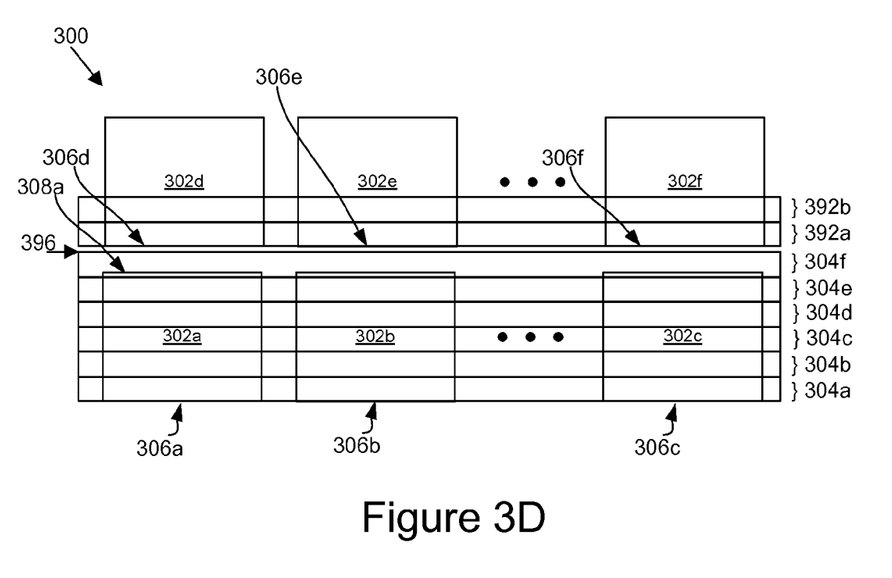
FIG. 3D illustrates a plurality of scanned swaths that have die-equivalent patch images in more than one swath in accordance with a second implementation of the present invention.

In a second implementation, die-equivalent patches of the entire set of scanned swaths for all the dies, which are designed to be identical, are processed together after the reticle is imaged. Although this second implementation provides improved results over the first implementation for single swath die-equivalent patches as further described below, this second implementation includes techniques for carefully positioning the swath scans relative to the dies. FIG. 3D illustrates a plurality of scanned swaths that have die-equivalent patch images in more than one swath in accordance with a second implementation of the present invention. As shown, the scanned swaths are positioned relative to the dies so that die-equivalent patch images are achieved across multiple swaths. For example, swaths 392a and 304a include a first set of die-equivalent patch images for dies (e.g., 302a~302f), while swaths 392b and 304b include a second set of die-equivalent patch images for dies (e.g., 302a~302f).

Figure 4:
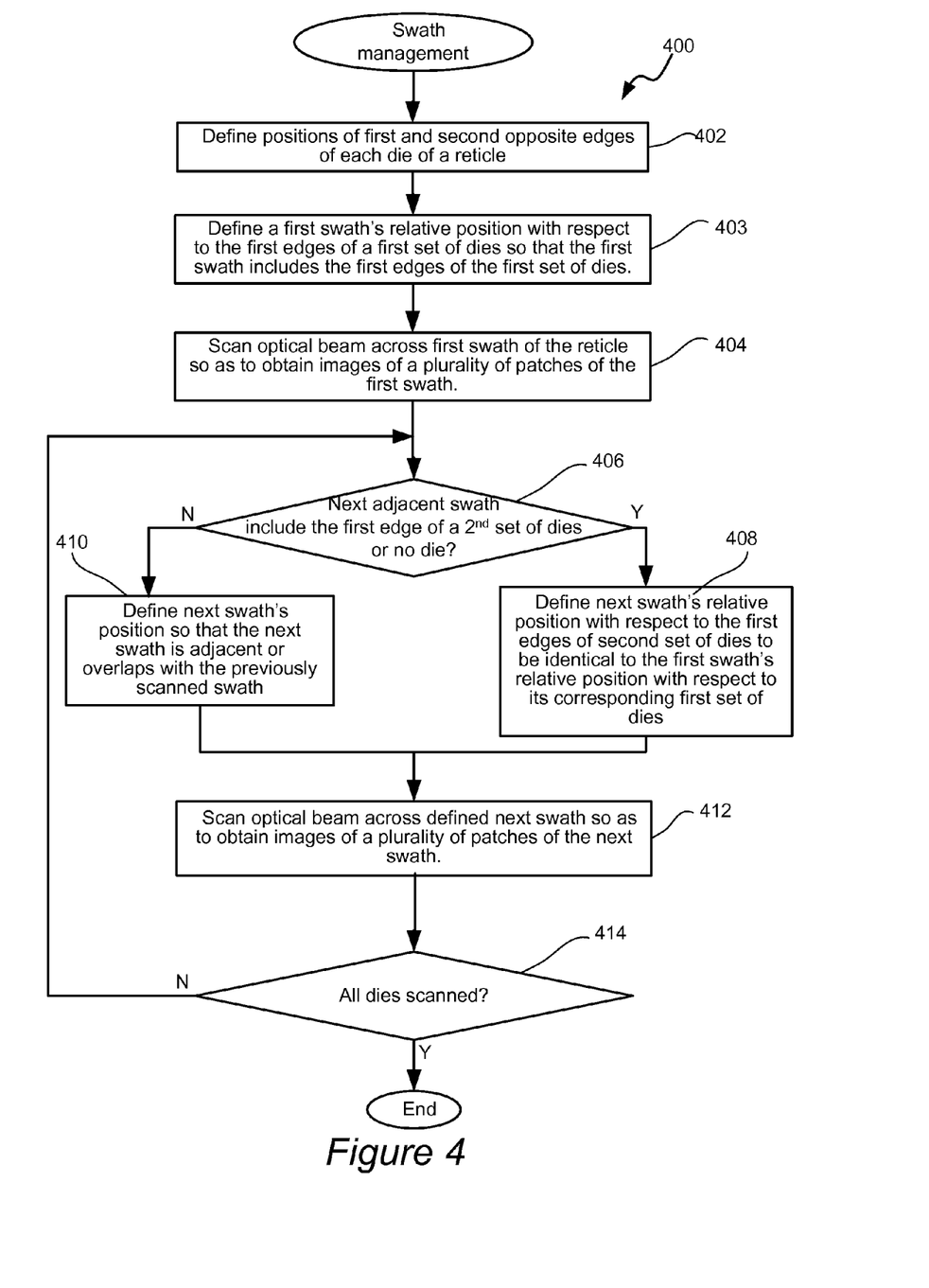
FIG. 4 is a flow chart illustrating a procedure for swath management for achieving die-equivalent patch images in accordance with a second implementation of the present invention.

FIG. 4 is a flow chart illustrating a procedure for swath management for achieving die-equivalent patch images across multiple scanned swaths. As shown, positions of first and second opposite edges of each identical die of a reticle may be defined in operation 402. In general, the inspection tool may be set up with information regarding each die's extent, die offsets, and an array size.

Figure 5:
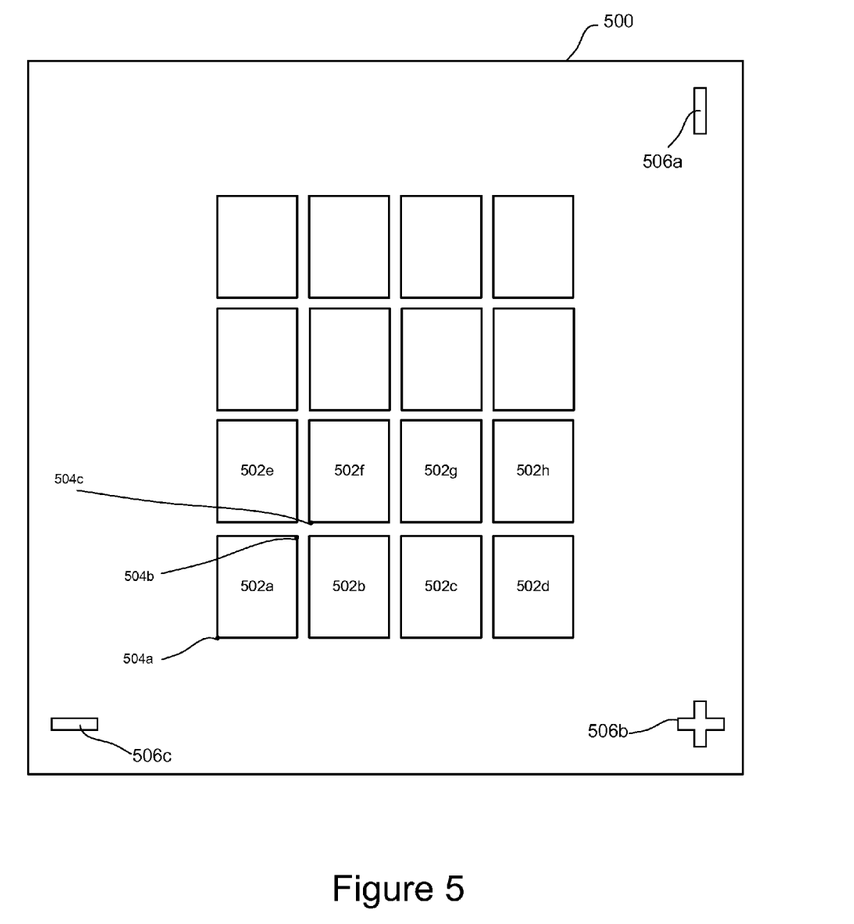
FIG. 5 illustrates a reticle having an array of dies for which an extent, offset, and array size are defined during a setup procedure in accordance with one example implementation of the present invention.

FIG. 5 illustrates a reticle 500 having an array of dies (e.g., 502a~h) for which an extent, offset, and array size are defined with respect to an inspection tool in accordance with one example implementation of the present invention. In a specific implementation, a setup process for an inspection tool may first include a mechanism for aligning a reticle in the tool. The reticle may be positioned by a user with respect to any suitable number and type of alignment marks, such as 506a~c, on the reticle so as to align the reticle and define a particular coordinate system for the reticle scan.

Through a setup process for the inspection tool, a user may select points 504a and 504b to define the extent of a first die 502a, as well as all the other dies, in the array. The user may also select point 504c to define an x and y offset with respect to the first die 502a. Other points (not shown) may also be selected to define extents and offsets. The array size may be input by the user into the inspection tool.

The inspection tool may use the defined die extent, die offsets, and array size to automatically define each swath position. Referring back to FIG. 4, a first swath's relative position with respect to the first edges of a first set of dies may be defined so that the first swath includes the first edges of the first set of dies in operation 403. In the example of FIG. 3D, the first swath 304a is defined relative to the bottom edges (e.g., 306a~306c) of the first set of dies (e.g., 302a~302c). The first swath may also be defined relative to any other equivalent positions of the first set of dies. A swath may generally be defined with respect to a particular die position by the inspection tool automatically initiating a scan at a particular swath position.

The optical beam of the inspection tool may then be scanned across the first swath of the reticle so as to obtain images of a plurality of patches of the first swath in operation 404. In one example, an optical beam may scan across the reticle and intensity values may be collected for each pixel or point in each patch of the first swath as such beam scans across each patch. Said in another way, the inspection tool may be operable to detect and collect reflected and/or transmitted light as an incident optical beam scans across each patch of the first swath. Light is collected in response to this incident beam from a plurality of points or subareas of each patch of the first swath.

In the example of FIG. 3D, first swath 304a includes a first edge 306a of die 302a, a first edge 306b of die 302b, and a first edge 306c of die 302c. Each die also has a second opposite edge (e.g., 308a). After the first swath is scanned, it may then be determined whether a next adjacent swath would include the first edges of a second set of dies or contain no dies in operation 406. If the first edge of a second set of dies has not yet been reached, the next swath's position may be defined so that the next swath is adjacent or overlaps with the previously scanned swath in operation 410. The optical beam is also scanned across this defined next swath so as to obtain images of a plurality of patches of the next swath in operation 412. It may then be determined whether all the dies have been scanned in operation 414. If not, next swaths continue to be defined and scanned until all the dies are scanned and the reticle scan is complete.

For instance, the next adjacent swath that is defined and scanned after the first swath 304a in FIG. 3D is swath 304b, which has not reached the first edges 306d~306e of the second set of dies 302d~302f. In this illustration, the next swath 304b is positioned adjacent to the first swath 304a. Swaths 304c~304f are sequentially defined and scanned as next swaths, which are each positioned adjacent to the previously scanned swath, and these next swaths are sequentially scanned with the inspection tool's optical beam to obtain patch images.

If adjacent swaths would continue to be scanned after swath 304g is scanned (e.g., 304h~304l) as in the first implementation of FIG. 3A, the patch images of the second set of dies (e.g., 302d~302f) would not be die-equivalent to the first set of dies (e.g., 302a~302c). For example, the patch images of swath 304g are not aligned to the first edges of the second set of dies 302d~f in the same way that the patch images of the first swath 304a are aligned to the first edges of the first set of dies 302a~c.

Thus, the illustrated second implementation includes repositioning of the next scan when a new set of dies are to be scanned. If the first edges of a second set of dies will be reached in the next scan, the next swath's relative position is defined with respect to the first edges of second set of the dies to be identical to the first swath's relative position with respect its respective dies in operation 408. After swath 304f is scanned, the next swath to be scanned is defined as swath 392a (FIG. 3D), which aligns to the first edges 306d~f of the second set of dies 302d~f. The procedure 400 repeats until the last swath is scanned.

Referring back to FIG. 2, an integrated value for an image characteristic, such as intensity, may be determined for each patch (or multiple patches) in operation 204. FIG. 3C is a diagrammatic illustration of multiple intensity data sets that corresponds to multiple local areas (e.g., 372a~372f) of each patch of a swath of the reticle. In certain implementations, an average or median intensity value may be determined for each patch or set of two or more patches. As shown, multiple intensity values (e.g., 372a, 372b, 372c, 372d, 372e, and 372f) correspond to multiple pixels or points of a particular patch 352a of a particular swath of a reticle. For example, intensity data set 352a corresponding to a patch of the reticle may include intensity values 26, 25, 25, 25, 24, 25, etc. All of the intensity values for each patch may be averaged together to determine an average intensity value (e.g., 25) for such patch.

For each test patch, a reference value is determined based from the integrated values of the test patch's die-equivalent patches in operation 206. For each test patch, a difference value between the determined integrated value of such test patch and its corresponding reference value can then be determined in operation 208. A delta map may then be generated based on the difference values that are determined for the patch images in operation 209. The delta map indicates any variation between a pattern characteristic of a particular patch and an average or median pattern characteristic of the particular patch's die-equivalent patches with optional exclusion of outlier patches.

Embodiments of a delta map can take any suitable form. For example, the delta map can be represented textually as a list of difference or "delta" values for each patch of the reticle.

For instance, each delta value may be listed alongside corresponding reticle patch coordinates. The map can optionally or additionally be represented by a metric, such as the standard deviation or variance of the difference values in operation 210. Alternatively or additionally, a delta map may be represented visually so that different delta values or ranges are shown in different visual ways, such as differently colored reticle patches, different bar graph heights, different graph values, or 3-dimensional representations, etc. The delta values may also be normalized.

When die-equivalent patches from a single swath (or a small number of patches) are processed to form a delta map, "false" echo effects may be generated in non-defective patches from a defective patch. For example, if an intensity value of a defective single patch differs from an average of the other non-defective patches, the defective patch will also cause the average of subsets of the non-defective patch images to increase or decrease by a small amount when each of the non-defective patch images is being assessed with respect to its die-equivalent other non-defective patch images and defective patch image. This small increase or decrease in the reference value affects the difference value for each non-defective patch image. Of course, the defective patch image will have a larger difference with a sign that is opposite the echo effect difference of the other non-defective patch images. Although these echo effects may not be a significant issue when other patch images have relatively large variance, the delta map may be noisier.

One solution to the echo effect, as well as other outlier issues, is to exclude or down weight certain outlier integrated intensity values of the die-equivalent patches when determining the reference value of the die-equivalent patches. Any suitable technique may be used to exclude or down weight outlier values from each reference value calculation. In a specific example, the median value (instead of the average value) of the other die-equivalent patches is used as the reference value. The median will be less influenced by outlier values from one or more defective region and will therefore have less corruption of the reference value by one or more defective regions.

Similarly, integrated intensity values of outlier patch images may be automatically excluded from the calculation for determining each reference value. One way may include eliminating integrated intensity values from the reference value calculation of each patch that has a value that exceeds a predefined threshold. In another example, integrated intensity values that are more than a predefined number of standard deviations from the average of the die-equivalent values may be excluded from each reference value determination. In one example, any integrated value has more than 5 sigma standard deviations may be excluded from a reference value calculation. In other embodiments, 3 sigma or 4 sigma intensity values may be excluded from the reference value determination.

The echo effect may be reduced and scaled down in relation to 1/N, where N is the number of dies used to determine each reference value. In some implementations, the echo effect can be significantly reduced by using all the other dies on a reticle, instead of a single row or swath of dies, to obtain a reference value so that more dies are averaged together. Even when all the other dies on a reticle are used to determine a reference value, a reticle that has a low number of dies will to have a smaller echo effect than a reticle that has a low number of dies.

In general, intensity values for different regions (such as the pixels of a patch) corresponding to the reflected light may also be combined with the intensity values for the transmitted light before or after determining the average intensity value for each patch. For instance, an average of the reflected and transmitted intensity values may be determined for each point or pixel. Alternatively, the averages may be calculated separately for the reflected and transmitted intensity values of a patch. The separately calculated reflected average and transmitted average for each patch may also be combined or averaged together. In one example implementation, the reflected (R) and transmitted (T) values different regions may be combined by (T−R)/2.

Reflected light generally responds differently to noise sources than transmitted light. For example, a surface roughness affects the reflected light and not the transmitted light. In general, transmitted and reflected light modes both contain the CD signal but have different (uncorrelated) noise sources. Thus, the two modes can be combined to potentially achieve a higher signal-to-noise ratio than either mode would achieve individually. In some cases, R and T signals for particular regions may have a same sign, instead of an opposite sign, which may indicate that the results are inconsistent in the associated regions and may not be trustworthy. Thus, the combination of R and T could be down-weighted in such regions or removed from the computation if insufficiently trustworthy.

In other embodiments, a reflected delta map may be generated using reflected intensity values, and a transmitted delta map may be generated using transmitted intensity values. In a specific technique, the reflected and transmitted delta maps are averaged together to form a combined reflected and transmitted delta map. For instance, the reflected difference value (R) and transmitted difference value (T) of each patch may be averaged together. Since the R and T delta values have an opposite sign, the averaging is performed by the equation (T−R)/2 so that the R and T delta values do not cancel each other out. That is, subtracting the two maps effectively adds the signals together.

Since the noise sources are different for T and R, the noise can tend to be averaged out of the combined signal. In other embodiments, certain noise sources may have a much larger effect on one of the R or T delta maps. For instance, when a haze is formed over the reticle over time, the R delta map will be significantly affected, while the T delta map is not. Thus, if the R and T delta maps were simply averaged together, the intensity changes caused by the haze would not be factored out of the combined delta map. In another technique, the reflected delta values can be weighted differently than the transmitted delta values based on any suitable noise indicator, such as how much the patch's intensity value varies from the average of the die-equivalent patches. In a specific implementation, the combined delta map can be formed using an inverse variance weighting. The following equation may be used to determine a combined reflected and transmitted delta map:

$$(1/(\sigma_T^2+\sigma_R^2))(\sigma_T^2 \Delta I_R/I_R - \sigma_R^2 \Delta I_T/I_T)$$

$\Delta I_R/I_R$ is the reflected delta value expressed as a percentage change; $\Delta I_T/I_T$ is the transmitted delta value expressed as a percentage change; and $\sigma_R$ and $\sigma_T$ are standard deviations from the die-equivalent patches' average reflected and transmitted intensity, respectively.

Other combinations of reflected and transmitted integrated values with weighting that is based on one or more noise factors (fill factor, light calibration, etc.) may be used. The noise factors may be weighted separately or combined. Fill factor corresponds to pattern density. The pattern edges affect the signal so that if there are a lot of edges, the R or T signal may be stronger and visa versa. Likewise, the R or T signal may be affected differently based on light calibration levels.

Defects may then be detected based on the delta map or a statistics map in operation 211. For instance, it may be determined whether any difference intensity value or delta value above a predefined threshold. Instead of using an absolute threshold to defect CD defects, the threshold can be based on the amount variance from the average. For instance, delta values that deviate by more than a certain percentage from the average are defined as defects. For instance, a delta intensity of 1 grayscale may be defined as a defect if the corresponding die-equivalent patches' intensity mean is 100 grayscales. Delta intensity values that vary more than a certain number of standard deviations may also be defined as defects.

After defects are detected, it may then be determined whether the reticle passes inspection based on such map in operation 212. If an intensity variation is above the predefined or statistics-based threshold, the corresponding patch may then be more carefully reviewed to determine whether the reticle is defective and can no longer be used. For instance, a SEM may be used to review the defective area to determine whether critical dimensions (CD's) are out of specification.

In alternative implementations, specific intensity changes in the delta intensity map can be associated with specific CD variations, which can then be determined to be in or out of specification. For instance, a 1% intensity variation may correlate to a 1% CD variation. Particular intensity changes may be associated with specific CD changes through calibration reticles having pattern areas with multiple known CD values that can be measured to determine intensity differences between different CD changes.

An out-of-specification CD variation would result in the reticle not passing the inspection. If the reticle fails inspection, the reticle may be discarded or repaired or the photolithography process adjusted in operation 214. For instance, certain defects can be cleaned from the reticle. After repair, a new reference inspection may be performed on the cleaned reticle and the procedure repeated.

The photolithography process may also be adjusted based on the delta map. In one implementation, the delta value, $\Delta I/I$, is related to the fractional dose correction, $\Delta D/D$, by $\Delta I/I = -\Delta D/D$. Dose correction based on intensity variation may be determined by the DoseMapper™ methodology available from ASML of Veldhoven, the Netherlands or the CDC correction methodology available from Zeiss of Germany.

Certain delta map embodiments illustrate intensity average changes across the different regions of the reticle. For instance, a delta map corresponds to how much light on average is transmitted through or is reflected from specific areas of the reticle. These delta maps illustrate average spatial variation without having to resolve defects on a fine scale resolution. A delta map may be generated and applied to non-repeating reticle features, as well as repeating reticle features.

The patch portions may be any size and shape, depending on the particular system and application requirements. Although certain embodiments are described with reference to sequentially scanning across rectangular swaths that are aligned perpendicular to the swath scan direction, the reticle may be scanned in any suitable manner. Alternatively, the images may be obtained by scanning the reticle with any suitable pattern, such as a circular or spiral pattern, with differently shaped swaths, as long as the swaths are positioned to achieve die-equivalent patch images. Of course, the sensors may have to be arranged differently (e.g., in a circular pattern) and/or the reticle may be moved differently (e.g., rotated) during scanning in order to scan a circular or spiral shape from the reticle.

In the example illustrated below, as the reticle moves past the sensors, light is detected from a rectangular region (herein referred to as a "swath") of the reticle and such detected light is converted into multiple intensity values at multiple points in each patch. In this embodiment, the sensors of the scanner are arranged in a rectangular pattern to receive light that is reflected and/or transmitted from the reticle and generate therefrom a set of intensity data that corresponds to a swath of patches of the reticle. In a specific example, each swath can be about 1 million pixels wide and about 1000 to 2000 pixels high, while each patch can be about 2000 pixels wide and 1000 pixels high.

Intensity values for each patch may be obtained using an optical inspection tool that is set up in any suitable manner. The optical tool is generally set up with a set of operating parameters or a "recipe". Recipe settings may include one or more of the following settings: die extent, die array size, die offsets, a setting for scanning the reticle in a particular pattern, pixel size, a setting for grouping adjacent signals from single signals, threshold values, a focus setting, an illumination or detection aperture setting, an incident beam angle and wavelength setting, a detector setting, a setting for the amount of reflected or transmitted light, aerial modeling parameters, etc.

Both transmitted and reflected light may be collected by the inspection tool. It is also preferable that the inspection light levels are properly calibrated and compensated.

The inspection tool may be generally operable to convert such detected light into detected signals corresponding to intensity values. The detected signals may take the form of an electromagnetic waveform having amplitude values that correspond to different intensity values at different locations of the reticle. The detected signals may also take the form of a simple list of intensity values and associated reticle point coordinates. The detected signals may also take the form of an image having different intensity values corresponding to different positions or scan points on the reticle. A reticle image may also be generated after all the positions of the reticle are scanned and converted into detected signals, or potions of a reticle image may be generated as each reticle portion is scanned with the final reticle image being complete after the entire reticle is scanned.

The inspection tool may be setup in a high resolution imaging mode or an aerial imaging mode. That is, the detected signals may take the form of high resolution images or low resolution aerial images. In general, the optics of the photolithography tool are emulated so as to produce an aerial image based on the detected signals from the reticle. For instance, a NA (numerical aperture) for a high resolution mode is typically between about 0.5 and 0.9, while a NA for an aerial imaging (low resolution) mode is typically between about 0.1 and 0.35.

There may be some advantages to operating in the aerial imaging mode for more accurate use of the delta map for CD correction methods, such as the DoseMapper™ methodology available from ASML of Veldhoven, the Netherlands and the CDC correction methodology available from Zeiss of Germany. The delta value, API, is related to the fractional dose correction, $\Delta D/D$, by $\Delta I/I = -\Delta D/D$. This relationship may be more accurately correct for aerial inspection modes than for high resolution modes, but may suffice in both modes.

The incident light or detected light may be passed through any suitable spatial aperture to produce any incident or detected light profile at any suitable incident angles. By way of examples, programmable illumination or detection apertures may be utilized to produce a particular beam profile, such as dipole, quadrapole, quasar, annulus, etc. In a specific example, Source Mask Optimization (SMO) or any pixelated illumination technique may be implemented.

The data for the detected signals for each set of one or more patches may be sent to parallel patch processors. For instance, the intensity values for a first patch may be sent to a first processor, and the intensity values for a second patch may be sent to a second processor. Alternatively, the data for a predefined number of patches may be sent to individual patch processors.

Each processor may determine and store average patch intensity values for each set of one or more patches. For instance, each processor may determine an average of one patch or an average for each set of multiple patches. The number of patches for which an average is determined, of course, affects the sampling granularity. That is, a higher number of patches for each average calculation is associated with a lower sampling number. However, noise is reduced as more patches are used to determine each average.

In one example implementation of the present invention, each patch (1 k×2 k) contains about 2 million pixels that are scanned to obtain intensity values for all 2 million points of each pixel. If an average is obtained for each patch, 2 million points are sampled. In another example, averaging the points in 2 patches results in 1 million points being sampled for each 2-patch grid. In effect, a larger patch that is 2 k×2 k may be used. Other patch sizes can be used for the techniques of the present invention.

The patches may be initially interpolated to a grid that has die-equivalent grid points before performing the difference to find the delta signal. In another implementation, the delta values are first determined before being interpolated to a grid. Grid interpolation may be performed so as to generate output data with a desired resolution. For example, a lower resolution set of data may be obtained by averaging and interpolating patches (e.g., from a 55 μm by 11 μm patch to a 200 μm by 200 μm patch), and this lower resolution can reduce noise and the size of the data output file.

Certain embodiments of the present invention may be applied to non-repeating logic patterns, as well as repeating patterns. Since intensity maps are generated using die-equivalent patches, rather than for repeating cell portions, intensity variations between die equivalent patches can be found for patches that do not form part of a repeating pattern.

Figure 6:
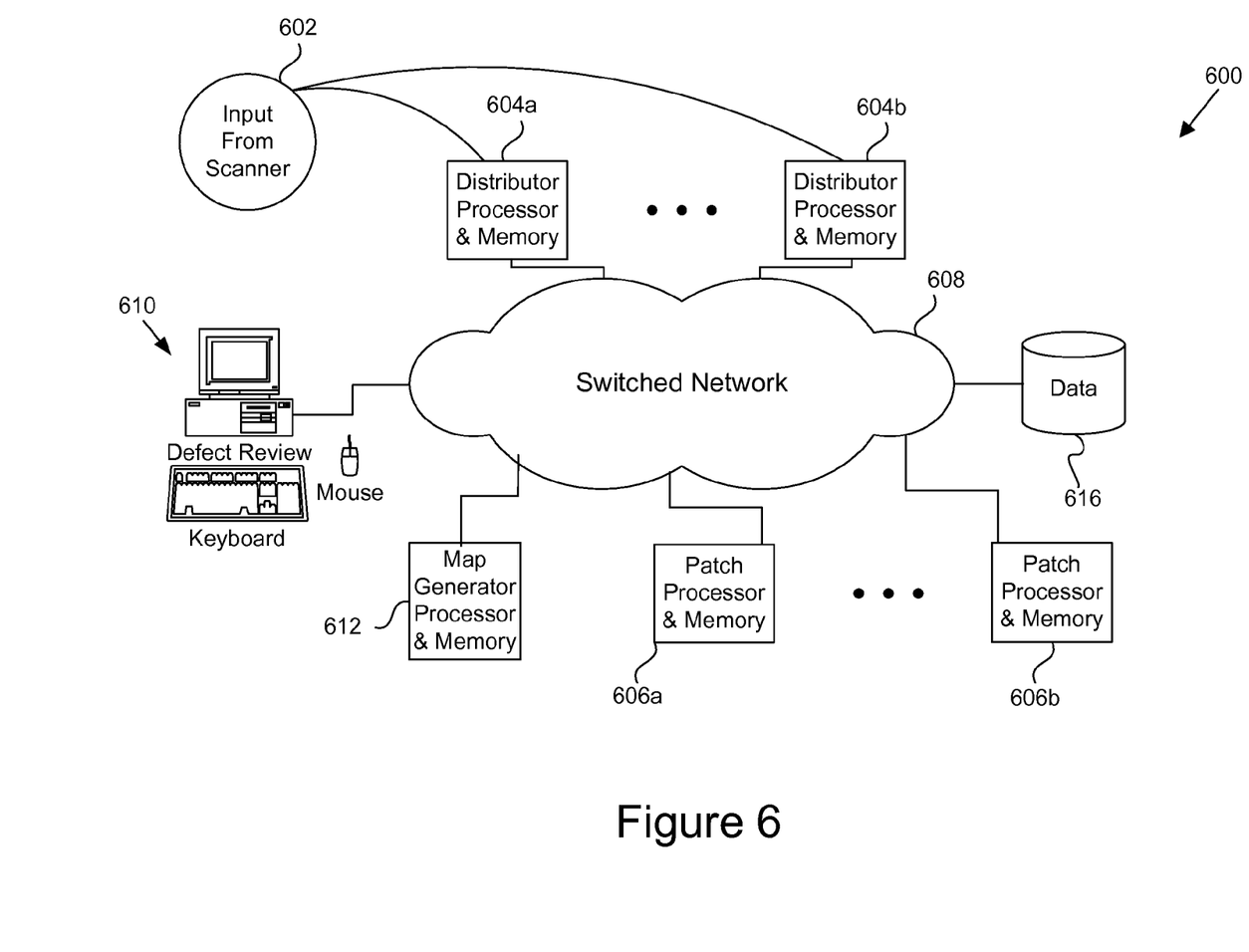
FIG. 6 is a diagrammatic representation of an example inspection system in which techniques of the present invention may be implemented

Techniques of the present invention may be implemented in any suitable combination of hardware and/or software. FIG. 6 is a diagrammatic representation of an example inspection system 600 in which techniques of the present invention may be implemented. The inspection system 600 may receive input 602 from an inspection tool or scanner (not shown). The inspection system may also include a data distribution system (e.g., 604a and 604b) for distributing the received input 602, an intensity signal (or patch) processing system (e.g., patch processors and memory 606a and 606b) for processing specific portions or patch images of received input 602, a map generator system (e.g., Map Generator Processor and Memory 612) for generating a delta map, a network (e.g., switched network 608) for allowing communication between the inspection system components, an optional mass storage device 616, and one or more inspection control and/or review stations (e.g., 610) for reviewing the delta maps. Each processor of the inspection system 600 typically may include one or more microprocessor integrated circuits and may also contain interface and/or memory integrated circuits and may additionally be coupled to one or more shared and/or global memory devices.

The scanner or data acquisition system (not shown) for generating input data 602 may take the form of any suitable instrument (e.g., as described further herein) for obtaining intensity signals or images of a reticle. For example, the scanner may construct an optical image or generate intensity values of a portion of the reticle based on a portion of detected light that is reflected, transmitted, or otherwise directed to one or more light sensors. The scanner may then output the intensity values or image may be output from the scanner.

Intensity or image data 602 can be received by data distribution system via network 608. The data distribution system may be associated with one or more memory devices, such as RAM buffers, for holding at least a portion of the received data 602. Preferably, the total memory is large enough to hold an entire swath of data. For example, one gigabyte of memory works well for a swath that is 1 million by 1000 pixels or points.

The data distribution system (e.g., 604a and 604b) may also control distribution of portions of the received input data 602 to the processors (e.g. 606a and 606b). For example, data distribution system may route data for a first patch to a first patch processor 606a, and may route data for a second patch to patch processor 606b. Multiple sets of data for multiple patches may also be routed to each patch processor.

The patch processors may receive intensity values or an image that corresponds to at least a portion or patch of the reticle. The patch processors may each also be coupled to or integrated with one or more memory devices (not shown), such as DRAM devices that provide local memory functions, such as holding the received data portion. Preferably, the memory is large enough to hold data that corresponds to a patch of the reticle. For example, eight megabytes of memory works well for intensity values or an image corresponding to a patch image that is 512 by 1024 pixels. Alternatively, the patch processors may share memory.

Each set of input data 602 may correspond to a swath of the reticle. One or more sets of data may be stored in memory of the data distribution system. This memory may be controlled by one or more processors within the data distribution system, and the memory may be divided into a plurality of partitions. For example, the data distribution system may receive data corresponding to a portion of a swath into a first memory partition (not shown), and the data distribution system may receive another data corresponding to another swath into a second memory partition (not shown). Preferably, each of the memory partitions of the data distribution system only holds the portions of the data that are to be routed to a processor associated with such memory partition. For example, the first memory partition of the data distribution system may hold and route first data to patch processor 606a, and the second memory partition may hold and route second data to patch processor 606b.

The data distribution system may define and distribute each set of data of the data based on any suitable parameters of the data. For example, the data may be defined and distributed based on the corresponding position of the patch on the reticle. In one embodiment, each swath is associated with a range of column positions that correspond to horizontal positions of pixels within the swath. For example, columns 0 through 256 of the swath may correspond to a first patch, and the pixels within these columns will comprise the first image or set of intensity values, which is routed to one or more patch processors. Likewise, columns 257 through 512 of the swath may correspond to a second patch, and the pixels in these columns will comprise the second image or set of intensity values, which is routed to different patch processor(s).

Figure 7A:
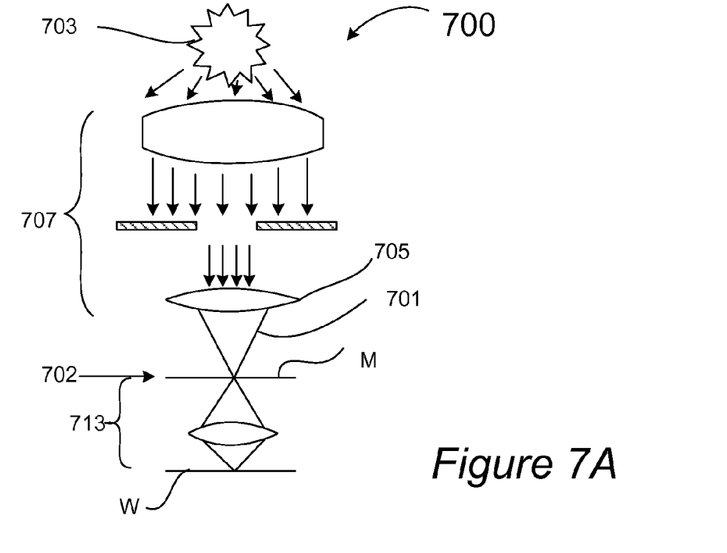
FIG. 7A is a simplified schematic representation of a lithographic system for transferring a mask pattern from a photomask onto a wafer in accordance with certain embodiments.

FIG. 7A is a simplified schematic representation of a typical lithographic system 700 that can be used to transfer a mask pattern from a photomask M onto a wafer W in accordance with certain embodiments. Examples of such systems include scanners and steppers, more specifically PAS 5500 system available from ASML in Veldhoven, Netherlands. In general, an illumination source 703 directs a light beam through an illumination optics 707 (e.g., lens 705) onto a photomask M located in a mask plane 702. The illumination lens 705 has a numeric aperture 701 at that plane 702. The value of the numerical aperture 701 impacts which defects on the photomask are lithographic significant defects and which ones are not. A portion of the beam that passes through the photomask M forms a patterned optical signal that is directed through imaging optics 713 and onto a wafer W to initiate the pattern transfer.

Figure 7B:
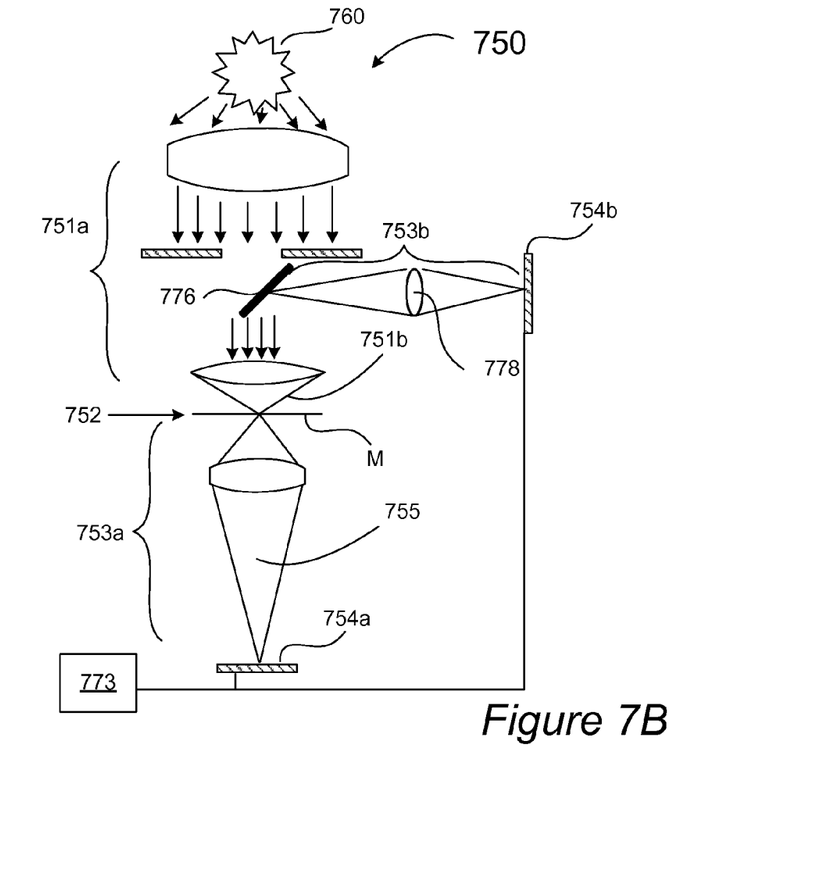
FIG. 7B provides a schematic representation of a photomask inspection apparatus in accordance with certain embodiments.

FIG. 7B provides a schematic representation of an example inspection system 750 that has illumination optics 751a includes an imaging lens with a relative large numerical aperture 751b at a reticle plane 752 in accordance with certain embodiments. The depicted inspection system 750 includes detection optics 753a and 753b, including microscopic magnification optics designed to provide, for example, 60-200× magnification or more for enhanced inspection. For example, numerical aperture 751b at the reticle plane 752 of the inspection system may be considerable greater than the numerical aperture 701 at the reticle plane 702 of the lithography system 700, which would result in differences between test inspection images and actual printed images. However, the inspection tool may also include optical elements for emulating the lithography system by generating aerial images with a smaller numerical aperture.

The inspection techniques described herein may be implemented on various specially configured inspection systems, such as the one schematically illustrated in FIG. 7B. The illustrated system 750 includes an illumination source 760 producing a light beam that is directed through illumination optics 751a onto a photomask M in the reticle plane 752. Examples of light sources include lasers or filtered lamps. In one example, the source is a 193 nm laser. As explained above, the inspection system 750 may have a numerical aperture 751b at the reticle plane 752 that may be greater than a reticle plane numerical aperture (e.g., element 701 in FIG. 7A) of the corresponding lithography system. The photomask M to be inspected is placed on a mask stage at the reticle plane 752 and exposed to the source.

The patterned image from the mask M is directed through a collection of optical elements 753a, which project the patterned image onto a sensor 754a. In a combination reflecting and transmitting system, optical elements (e.g., beam splitter 776 and detection lens 778) also direct and capture the reflected light onto sensor 754b. Suitable sensors include charged coupled devices (CCD), CCD arrays, time delay integration (TDI) sensors, TDI sensor arrays, photomultiplier tubes (PMT), and other sensors.

The illumination optics column may be moved respect to the mask stage and/or the stage moved relative to a detector or camera by any suitable mechanism so as to scan patches of the reticle. For example, a motor mechanism may be utilized to move the stage. The motor mechanism may be formed from a screw drive and stepper motor, linear drive with feedback position, or band actuator and stepper motor, by way of examples.

The signals captured by each sensor (e.g., 754a and/or 754b) can be processed by a computer system 773 or, more generally, by one or more signal processing devices, which may each include an analog-to-digital converter configured to convert analog signals from each sensor into digital signals for processing. The computer system 773 typically has one or more processors coupled to input/output ports, and one or more memories via appropriate buses or other communication mechanisms.

The computer system 773 may also include one or more input devices (e.g., a keyboard, mouse, joystick) for providing user input, such as inputting array size and die extent and offsets, such as changing focus and other inspection recipe parameters. The computer system 773 may also be connected to the stage for controlling, for example, a sample position (e.g., focusing and scanning) and connected to other inspection system components for controlling other inspection parameters and configurations of such inspection system components.

The computer system 773 may be configured (e.g., with programming instructions) to provide a user interface (e.g., a computer screen) for displaying delta maps, resultant intensity values, images, and other inspection results. The computer system 773 may be configured to analyze intensity, phase, and/or other characteristics of reflected and/or transmitted sensed light beam. The computer system 773 may be configured (e.g., with programming instructions) to provide a user interface (e.g., on a computer screen) for displaying resultant delta maps, intensity values, images, and other inspection characteristics. In certain embodiments, the computer system 773 is configured to carry out inspection techniques detailed above Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

In certain embodiments, a system for inspecting a photomask includes at least one memory and at least one processor that are configured to perform techniques described herein. One example of an inspection system includes a specially configured TeraScan™ DUV inspection system available from KLA-Tencor of Milpitas, Calif.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A method of inspecting a photolithographic reticle, the method comprising:
with an optical inspection tool, obtaining a plurality of patch images of a plurality of patches of a plurality of dies of the reticle, wherein the dies are designed to be identical, and wherein the patch images are obtained so that each patch image is positioned relative to a same reference position within its respective die as another die-equivalent one of the patch images in each of a plurality of other ones of the dies;

for each patch image, determining an integrated value for an image characteristic of a plurality of sub-portions of such patch image;

for each patch image, determining a reference value based on the integrated values of the patch image's corresponding die-equivalent patch images;

for each patch image, determining a difference between that patch image's integrated value and an average or median value of the integrated values of the patch image's die-equivalent patch images whereby such difference indicates a difference between a pattern characteristic of any patch and an average or median pattern characteristic of its die-equivalent patches;

generating a delta map based on the determined difference for each patch image; and detecting defects on the reticle based on the delta map.

2. The method of claim 1, wherein the pattern characteristic is a critical dimension.

3. The method of claim 1, wherein the patch images are obtained by using the optical tool to scan an optical beam along a plurality of swaths that include all the dies of the reticle.

4. The method of claim 3, wherein each image patch's reference position corresponds to a die edge of such image patch's corresponding die and the patch images are obtained by positioning a portion of the swaths at the die edge a corresponding die.

5. The method of claim 1, wherein the patch images are obtained from a single swath selected from a plurality of swaths that were imaged with the optical tool by scanning an optical beam along each of the swaths, and wherein the single swath includes portions of a subset of all the dies of the reticle, wherein the subset of dies are aligned with each other and in a direction in which the optical beam scans along the single swath.

6. The method of claim 1, wherein the integrated value for each patch image is an average of a plurality of intensity values of the sub-portions of such patch image.

7. The method of claim 1, wherein the integrated value for each patch image is a median of a plurality of intensity values of the sub-portions of such patch image.

8. The method of claim 1, wherein each integrated value is an average of both reflected and transmitted intensity values from each corresponding patch image.

9. The method of claim 1, wherein the delta map indicates a standard deviation of each determined difference.

10. The method of claim 9, further comprising defining any standard deviations that is above a predefined threshold as a critical dimension variation defect.

11. The method of claim 1, wherein each determined difference includes a reflected intensity difference value and a transmitted difference value and wherein the delta map is generated by combining each reflected difference value with its corresponding transmitted difference value.

12. The method of claim 11, wherein combining each reflected difference value with its corresponding transmitted difference value is performed by averaging each reflected difference value with its corresponding transmitted difference value.

13. The method of claim 11, wherein combining each reflected difference value with its corresponding transmitted difference value includes weighting each reflected difference value differently from its corresponding transmitted difference value.

14. The method of claim 1, further comprising providing a dose correction for a photolithography process that uses the reticle based on the delta map.

15. The method of claim 1, wherein each reference value is determined by first excluding any integrated values that has a standard deviation that is greater than a predefined value from the reference value determination.

16. The method of claim 1, wherein the patch images are obtained by using the optical tool in an aerial mode.

17. An inspection system for inspecting a photolithographic reticle, the system comprising at least one memory and at least one processor that are configured to perform the following operations:

obtaining a plurality of patch images of a plurality of patches of a plurality of dies of the reticle, wherein the dies are designed to be identical, and wherein the patch images are obtained so that each patch image is positioned relative to a same reference position within its respective die as another die-equivalent one of the patch images in each of a plurality of other ones of the dies;

for each patch image, determining an integrated value for an image characteristic of a plurality of sub-portions of such patch image;

for each patch image, determining a reference value based on the integrated values of the patch image's corresponding die-equivalent patch images;

for each patch image, determining a difference between that patch image's integrated value and an average or median value of the integrated values of the patch image's die-equivalent patch images whereby such difference indicates a difference between a pattern characteristic of any patch and an average or median pattern characteristic of its die-equivalent patches;

generating a delta map based on the determined difference for each patch image; and detecting defects on the reticle based on the delta map.

18. The system of claim 17, wherein the pattern characteristic is a critical dimension.

19. The system of claim 17, wherein the patch images are obtained by using the system to scan an optical beam along a plurality of swaths that include all the dies of the reticle.

20. The system of claim 19, wherein each image patch's reference position corresponds to a die edge of such image patch's corresponding die and the patch images are obtained by positioning a portion of the swaths at the die edge a corresponding die.

21. The system of claim 17, wherein the patch images are obtained from a single swath selected from a plurality of swaths that were imaged with the optical tool by scanning an optical beam along each of the swaths, and wherein the single swath includes portions of a subset of all the dies of the reticle, wherein the subset of dies are aligned with each other and in a direction in which the optical beam scans along the single swath.

22. The system of claim 17, wherein the delta map indicates a standard deviation of each determined difference.

23. The system of claim 22, wherein the at least one memory and the at least one processor are further configured for defining any standard deviations that is above a predefined threshold as a critical dimension variation defect.

24. The system of claim 17, wherein each determined difference includes a reflected intensity difference value and a transmitted difference value and wherein the delta map is generated by combining each reflected difference value with its corresponding transmitted difference value.

25. The system of claim 24, wherein combining each reflected difference value with its corresponding transmitted difference value includes weighting each reflected difference value differently from its corresponding transmitted difference value.

26. A non-transitory computer readable medium having instruction stored thereon for performing the following operations:

with an optical inspection tool, obtaining a plurality of patch images of a plurality of patches of a plurality of dies of the reticle, wherein the dies are designed to be identical, and wherein the patch images are obtained so that each patch image is positioned relative to a same reference position within its respective die as another die-equivalent one of the patch images in each of a plurality of other ones of the dies;

for each patch image, determining an integrated value for an image characteristic of a plurality of sub-portions of such patch image;

for each patch image, determining a reference value based on the integrated values of the patch image's corresponding die-equivalent patch images;

for each patch image, determining a difference between that patch image's integrated value and an average or median value of the integrated values of the patch image's die-equivalent patch images whereby such difference indicates a difference between a pattern characteristic of any patch and an average or median pattern characteristic of its die-equivalent patches;

generating a delta map based on the determined difference for each patch image; and detecting defects on the reticle based on the delta map.

* * * * *